(12) United States Patent
List

(10) Patent No.: US 11,633,131 B2
(45) Date of Patent: Apr. 25, 2023

(54) DEVICE AND A METHOD FOR DETECTING AT LEAST ONE ANALYTE IN A BODY FLUID OF A USER

(71) Applicant: Roche Diabetes Care, Inc., Indianapolis, IN (US)

(72) Inventor: Hans List, Mannheim (DE)

(73) Assignee: Roche Diabetes Care, Inc., Indianapolis, IN (US)

(*) Notice: Subject to any disclaimer, the term of this patent is extended or adjusted under 35 U.S.C. 154(b) by 81 days.

(21) Appl. No.: 16/857,673

(22) Filed: Apr. 24, 2020

(65) Prior Publication Data
US 2020/0245907 A1 Aug. 6, 2020

Related U.S. Application Data

(63) Continuation of application No. PCT/EP2018/079455, filed on Oct. 26, 2018.

(30) Foreign Application Priority Data

Oct. 27, 2017 (EP) .................................... 17198924

(51) Int. Cl.
*A61B 5/1473* (2006.01)
*A61B 5/00* (2006.01)
(Continued)

(52) U.S. Cl.
CPC .......... *A61B 5/1473* (2013.01); *A61B 5/6849* (2013.01); *A61B 5/0031* (2013.01);
(Continued)

(58) Field of Classification Search
CPC ... A61B 5/1473; A61B 5/6849; A61B 5/0031; A61B 5/14532; A61B 5/14865; A61B 5/6833; A61B 2560/063
See application file for complete search history.

(56) References Cited

U.S. PATENT DOCUMENTS 5,413,690 A 5/1995 Kost et al.
5,762,770 A 6/1998 Pritchard et al.
(Continued)

FOREIGN PATENT DOCUMENTS

CN 101321494 A 12/2008
CN 103654772 A 3/2014
(Continued)

OTHER PUBLICATIONS

International Search Report and Written Opinion of the International Searching Authority, PCT/EP2018/079455, dated Feb. 4, 2019, 11 pages.

*Primary Examiner* — Nathan J Jenness
*Assistant Examiner* — Liam A Wallace
(74) *Attorney, Agent, or Firm* — Bose McKinney & Evans LLP

(57) ABSTRACT

A contact assembly for electrically interconnecting at least two modules is disclosed. The contact assembly has a first module having a first contact pad and a second module having a second contact pad. The first and second contact pads are arranged nonparallel to one another. One of the first and second contact pads exerts pressure on an electrically conductive elastomer to thereby deform it, and the deformation results in the other one of the first and second contact pads being contacted by the electrically conductive elastomer. An electrochemical sensor may be part of the first module and an electronics assembly may be part of the second module. An insertion needle may also be provided to insert the sensor transcutaneously. Associated methods are disclosed.

17 Claims, 5 Drawing Sheets

(51) Int. Cl.
   *A61B 5/145*    (2006.01)
   *A61B 5/1486*   (2006.01)

(52) U.S. Cl.
   CPC ....... *A61B 5/14532* (2013.01); *A61B 5/14546* (2013.01); *A61B 5/14865* (2013.01); *A61B 5/6833* (2013.01); *A61B 2560/063* (2013.01)

(56) References Cited

U.S. PATENT DOCUMENTS

| | | |
|---|---|---|
| 5,798,031 A | 8/1998 | Charlton et al. |
| 6,129,823 A | 10/2000 | Hughes et al. |
| 2005/0013731 A1 | 1/2005 | Burke et al. |
| 2008/0288026 A1 | 11/2008 | Cross et al. |
| 2013/0333094 A1 | 12/2013 | Rogers et al. |
| 2014/0011391 A1 | 1/2014 | Hung et al. |
| 2014/0081116 A1 | 3/2014 | Nakashima et al. |
| 2017/0290546 A1* | 10/2017 | Antonio ............. A61B 17/3468 |

FOREIGN PATENT DOCUMENTS

| | | | |
|---|---|---|---|
| CN | 105283122 A | 1/2016 | |
| EP | 2 499 969 A1 | 9/2012 | |
| EP | 2 322 094 B1 | 3/2014 | |
| EP | 1 075 209 B1 | 10/2014 | |
| WO | WO 2011063259 A2 | 5/2011 | |
| WO | WO 2013/152090 A2 | 10/2013 | |
| WO | WO-2017085247 A1 * | 5/2017 | ......... A61B 5/14532 |

\* cited by examiner

DEVICE AND A METHOD FOR DETECTING AT LEAST ONE ANALYTE IN A BODY FLUID OF A USER

RELATED APPLICATIONS

This application is a continuation of PCT/EP2018/079455, filed Oct. 26, 2018, which claims priority to EP 17 198 924.7, filed Oct. 27, 2017, both of which are hereby incorporated herein by reference.

BACKGROUND

This disclosure relates to a contact assembly for interconnecting at least two modules and to a sensor device for detecting at least one analyte in a body fluid, the sensor device comprising the contact assembly. This disclosure further relates to a medical device. This disclosure further relates to a method for electrically interconnecting at least two modules and to a method for manufacturing a sensor device for detecting at least one analyte in a body fluid of a user. The devices and methods according to this disclosure may mainly be used for long-term monitoring of an analyte concentration in a body fluid, such as for long-term monitoring of a blood glucose level or of the concentration of one or more other types of analytes in a body fluid. This disclosure may be applied in the field of home care as well as in the field of professional care, such as in hospitals. Other applications are feasible.

BACKGROUND

Monitoring certain body functions, more particularly monitoring one or more concentrations of certain analytes, plays an important role in the prevention and treatment of various diseases. Without restricting further possible applications, this disclosure will be described in the following text with reference to blood-glucose monitoring. However, additionally or alternatively, this disclosure can also be applied to other types of analytes.

Blood glucose monitoring, besides by using optical measurements, specifically may be performed by using electrochemical biosensors. Examples of electrochemical biosensors for measuring glucose, specifically in blood or other body fluids, are known from U.S. Pat. Nos. 5,413,690 A, 5,762,770 A, 5,798,031 A, 6,129,823 A or U.S. Publication No. 2005/0013731 A1.

Continuous monitoring systems typically are transcutaneous systems or subcutaneous systems, wherein both expressions, in the following, will be used equivalently. This means that the actual sensor or at least a measuring portion of the sensor is arranged under the skin of the user. However, an evaluation and control part of the system (also referred to as a patch) is generally situated outside of the body of the user, outside of the human or animal body. There are numerous examples of continuous monitoring systems, such as described in EP 2 322 094 B1, WO 2013/152090 A2 or EP 1 075 209 B1.

EP 2 322 094 B1 discloses an analyte sensor assembly for measuring an analyte in a host. The analyte sensor assembly comprises a housing configured for mounting on a skin of a host. The analyte sensor further comprises a sensor comprising a distal portion and a proximal portion, wherein the distal portion is adapted to be inserted through the skin of the host, and wherein the proximal portion is operably connected to the housing. The analyte sensor further comprises an electronics unit configured for measuring an analyte in the host and being detachably connectable to the housing. The electronics unit is connected to the sensor via at least one electrical contact to form an electrical connection. The at least one electrical contact is sealed from moisture in an external environment by at least one elastomeric sealing member configured to seal the electrical connection when the electronics unit is detachably connected to the housing. Further the housing is adapted to house the electronics unit.

WO 2013/152090 A2 presents embodiments that relate generally to systems and methods for measuring an analyte in a host. More particularly, the presented embodiments provide sensor applicators and methods of use with push-button activation that implant the sensor, withdraw the insertion needle, engage the transmitter with the housing, and disengage the applicator from the housing, all in one smooth motion. Some embodiments contemplate engagement of the transmitter with the housing after release of the applicator.

EP 1 075 209 B1 discloses a sensor control unit comprising a housing adapted to removably receive a portion of an electrochemical sensor extending out of the skin and having at least one contact pad. The sensor control unit further comprises at least one conductive contacts configured for coupling to the at least one contact pad on the sensor. The sensor control unit further comprises an RF transmitter coupled to the at least one conductive contact for transmitting data obtained using the sensor. Further the housing is adapted for attaching to the skin, and the RF transmitter is disposed in the housing.

In EP 2499969 A1, systems and methods for measuring an analyte in a host are described. More particularly, systems and methods for transcutaneous measurement of glucose in a host are disclosed. The system can include an applicator, a mounting unit, and an electronics unit.

U.S. Publication No. 2014/011391 A1 describes an electrical connector including an insulative housing defining a receiving chamber for inserting a test chip, a number of contacts with resilient contacting portions extending into the receiving chamber, a metal shell enclosing the insulative housing and a slide mechanism mounted onto the insulative housing. The slide mechanism includes a slider through which the insulative housing extends and an elastic member compressed between the slider and the metal shell. The slider is slidable with respect to the insulative housing so as to withdraw the test chip from the receiving chamber.

Despite the advantages of the above-mentioned prior art documents, several technical challenges remain. Thus, typically, transcutaneous systems are worn by the user for a limited time period, for example for a time period from several hours to several months or typically several days to several weeks, or, more typically, one week. As a rule, the sensor is configured to be replaced more regularly than other components of the transcutaneous system, such as an electronics unit or transmitter. The sensor typically is part of a disposable group of components of the transcutaneous system. Consequently, cost-efficient and simple techniques for electrically contacting the sensor are required. Still, due to the fact that medical decisions such as the decision on an appropriate medication strongly depends on the sensor readings, the contacting of the sensor has to take place at a high precision and reliability.

SUMMARY

This disclosure teaches devices and methods which address the above-mentioned technical challenge. Specifically, a sensor device is taught for detecting at least one analyte in a body fluid of a user which implies a cost-efficient and simple electrical contacting of a sensor, which, still, provides a high degree of precision and reliability.

As used in the following, the terms "have," "comprise" or "include" or any arbitrary grammatical variations thereof are used in a non-exclusive way. Thus, these terms may both refer to a situation in which, besides the feature introduced by these terms, no further features are present in the entity described in this context and to a situation in which one or more further features are present. As an example, the expressions "A has B," "A comprises B" and "A includes B" may both refer to a situation in which, besides B, no other element is present in A (i.e., a situation in which A solely and exclusively consists of B) and to a situation in which, besides B, one or more further elements are present in entity A, such as element C, elements C and D or even further elements.

Further, it shall be noted that the terms "at least one," "one or more" or similar expressions indicating that a feature or element may be present once or more than once typically will be used only once when introducing the respective feature or element. In the following, in most cases, when referring to the respective feature or element, the expressions "at least one" or "one or more" will not be repeated, non-withstanding the fact that the respective feature or element may be present once or more than once. It shall also be understood for purposes of this disclosure and appended claims that, regardless of whether the phrases "one or more" or "at least one" precede an element or feature appearing in this disclosure or claims, such element or feature shall not receive a singular interpretation unless it is made explicit herein. By way of non-limiting example, the terms "contact pad," "module," "sensor," and "elastomer," to name just a few, should be interpreted wherever they appear in this disclosure and claims to mean "at least one" or "one or more" regardless of whether they are introduced with the expressions "at least one" or "one or more." All other terms used herein should be similarly interpreted unless it is made explicit that a singular interpretation is intended.

Further, as used in the following, the terms "preferably," "more preferably," "particularly," "more particularly," "specifically," "more specifically" or similar terms are used in conjunction with optional features, without restricting alternative possibilities. Thus, features introduced by these terms are optional features and are not intended to restrict the scope of the claims in any way. The invention may, as the skilled person will recognize, be performed by using alternative features. Similarly, features introduced by "in an embodiment of the invention" or similar expressions are intended to be optional features, without any restriction regarding alternative embodiments of the invention, without any restrictions regarding the scope of the invention and without any restriction regarding the possibility of combining the features introduced in such way with other optional or non-optional features of the invention.

In a first aspect, a contact assembly for electrically interconnecting at least two modules is disclosed. The contact assembly has at least one first contact pad comprised by a first one of the modules, in the following also referred to as "the first module," and at least one second contact pad comprised by a second one of the modules, in the following also referred to as "the second module." Therein, as in the following, the terms "first" and "second" are used as nomenclature only, without numbering or ranking.

The first contact pad and the second contact pad specifically may be arranged in a nonparallel fashion with respect to one another. Thus, an angle between the surface of the first contact pad and the surface of the second contact pad or an angle between surface normals of the first and second contact pads deviates from 0° and deviates from 180°, e.g., by at least 5°, by at least 10° or by at least 20°.

The contact assembly further comprises at least one electrically conductive elastomeric element (also referred to herein as "elastomer"). The contact assembly is arranged such that one of the first contact pad or the second contact pad, i.e., the first contact pad or the second contact pad, exerts a pressure onto the electrically conductive elastomer, thereby deforming the electrically conductive elastomer. By the deformation, the other one of the first contact pad or the second contact pad is contacted by the electrically conductive elastomer. In other words, the first contact pad or the second contact pad deforms the electrically conductive elastomer wherein, due to the deformation, the other contact pad, i.e., the second contact pad or the first contact pad, is electrically contacted, which, as an example, would not be the case without the deformation.

The term "contact assembly" as used herein is a broad term and is to be given its ordinary and customary meaning to a person of ordinary skill in the art and is not to be limited to a special or customized meaning. The term specifically may refer, without limitation, to an assembly comprising at least two elements which are electrically interconnected or intended to be electrically interconnected. In the following, these at least two elements specifically may be or may comprise at least one first contact pad comprised by the at least one first module and at least one second contact pad comprised by the at least one second module. The contact assembly further comprises the at least one electrically conductive elastomeric element. Thus, the term "contact assembly" specifically may refer to the contact assembly comprising at least the at least one first contact pad, the at least one second contact pad and the at least one electrically conductive elastomeric element. Optionally, the first and second modules may also be fully or at least partially considered as part of the contact assembly.

As further used herein, the term "module" is a broad term and is to be given its ordinary and customary meaning to a person of ordinary skill in the art and is not to be limited to a special or customized meaning. The term specifically may refer, without limitation, to an arbitrary element or device having a functionality, such as an electrical functionality. Specifically, as will be outlined in further detail below, the first module specifically may be or may comprise at least one sensor element (also referred to herein as "sensor") for electrochemically detecting the at least one analyte, and the second module specifically may be or may comprise at least one electronics unit (also referred to herein as "electronics" or "electronics assembly"), such as an electronics unit interacting with the sensor, e.g., an electronics unit comprising electronics for performing at least one electrochemical measurement using an analytical sensor, such as a transcutaneous sensor, and/or electronics for storing and/or transmitting analytical measurement data, e.g., to another device, a data management device or an evaluation device. Other embodiments of the modules, however, are feasible.

In a further aspect, a sensor device for detecting at least one analyte in a body fluid of a user is disclosed. The sensor device comprises the contact assembly according to any one of the preceding embodiments and/or according to any one of the embodiments disclosed in further detail below. Therein, the first module of the contact assembly comprises at least one sensor element for electrochemically detecting the at least one analyte. The sensor element has the at least one first contact pad of the contact assembly. Further, the second module of the contact assembly comprises at least one electronics unit. The electronics unit comprises the at least one second contact pad of the contact assembly.

The term "sensor device" as used herein is a broad term and is to be given its ordinary and customary meaning to a person of ordinary skill in the art and is not to be limited to a special or customized meaning. The term specifically may refer, without limitation, to an arbitrary element which is adapted to perform a process of detection and/or which is adapted to be used in the process of detection. Thus, the sensor device, by itself or in cooperation with one or more of the components, may specifically be adapted to determine the concentration of the at least one analyte and/or a presence of the at least one analyte.

The term "sensor element" (also referred to herein merely as "sensor" as already noted) as used herein is a broad term and is to be given its ordinary and customary meaning to a person of ordinary skill in the art and is not to be limited to a special or customized meaning. The term specifically may refer, without limitation, to an arbitrary element which is adapted to detect the at least one analyte in the body fluid of the user. The sensor element may fully or partially be arranged under the skin of the user. Particularly the sensor element may be fully or partially implantable in a body tissue of the user. The sensor element, as an example, may be or may comprise an electrochemical sensor element, such as an electrochemical glucose sensor. Specifically, the sensor element, as will be outlined in further detail below, may comprise one or more electrodes, such as one or more working electrodes having at least one test chemical for detecting the at least one analyte and one or more further electrodes, such as one or more reference electrodes and/or one or more counter electrodes. For potential embodiments of the sensor element, reference may be made to the known sensor elements as disclosed in the prior art documents given above or to one or more of the embodiments shown in further detail below.

The term "detection" as used herein is a broad term and is to be given its ordinary and customary meaning to a person of ordinary skill in the art and is not to be limited to a special or customized meaning. The term specifically may refer, without limitation, to a process of determining a presence and/or a quantity and/or a concentration of the at least one analyte. Thus, the detection may be or may comprise a qualitative detection, simply determining the presence of the at least one analyte or the absence of the at least one analyte, and/or may be or may comprise a quantitative detection, which determines the quantity and/or the concentration of the at least one analyte. As a result of the detection, at least one signal may be produced which characterizes an outcome of the detection, such as at least one measurement signal. The at least one signal specifically may be or may comprise at least one electronic signal such as at least one voltage and/or at least one current. The at least one signal may be or may comprise at least one analogue signal and/or may be or may comprise at least one digital signal. The sensor element specifically may be an electrochemical sensor.

As outlined above, the sensor element is configured for electrochemically detecting the at least one analyte. Thus, the sensor element specifically may be or may comprise an electrochemical sensor or an electrochemical sensor element. The term "electrochemically detecting" as used herein is a broad term and is to be given its ordinary and customary meaning to a person of ordinary skill in the art and is not to be limited to a special or customized meaning. The term specifically may refer to a detection of an electrochemically detectable property of the at least one analyte, such as an electrochemical detection reaction. Thus, for example, the electrochemical detection reaction may be detected by comparing one or more electrode potentials. The electrochemical sensor specifically may be adapted to and/or may be usable to generate at least one electrical sensor signal which directly or indirectly indicates the presence and/or the extent of the electrochemical detection reaction, such as at least one current and/or at least one voltage. The sensor element may comprise at least two electrodes, such as at least one working electrode and at least one counter electrode. The sensor element may further comprise at least one reference electrode.

The term "working electrode" as used herein is a broad term and is to be given its ordinary and customary meaning to a person of ordinary skill in the art and is not to be limited to a special or customized meaning. The term specifically may refer, without limitation, to an electrode being adapted for or being usable for performing at least one electrochemical detection reaction for detecting the at least one analyte in the body fluid. The working electrode may have at least one test chemical being sensitive to the at least one analyte to be detected.

The term "test chemical" as used herein is a broad term and is to be given its ordinary and customary meaning to a person of ordinary skill in the art and is not to be limited to a special or customized meaning. The term specifically may refer, without limitation, to an arbitrary material or a composition of materials adapted to change at least one detectable property in the presence of at least one analyte. This property may be an electrochemically detectable property. Specifically, the at least one test chemical may be a highly selective test chemical, which only changes the property if the at least one analyte is present in the body fluid whereas no change occurs if the at least one analyte is not present. The degree or change of the at least one property is dependent on the concentration of the at least one analyte in the body fluid, in order to allow a quantitative detection of the at least one analyte. As an example, the test chemical may comprise at least one enzyme, such as glucose oxidase and/or glucose dehydrogenase.

The term "counter electrode" as used herein is a broad term and is to be given its ordinary and customary meaning to a person of ordinary skill in the art and is not to be limited to a special or customized meaning. The term may refer, without limitations, to an electrode adapted for performing at least one electrochemical counter reaction and adapted for balancing a current flow required by the detection reaction at the working electrode.

The term "reference electrode" as used herein is a broad term and is to be given its ordinary and customary meaning to a person of ordinary skill in the art and is not to be limited to a special or customized meaning. The term may refer, without limitations, to an electrode adapted for providing a well-known counter reaction regardless of the detection reaction at the working electrode. The reference electrode may be adapted to provide a known current flow for comparative purposes.

However, additionally or alternatively, other types of sensor elements are possible in accordance with this disclosure. Such sensor elements may be one or more sensor elements for detecting a heart rate, such as by detecting appropriate movements due to a heartbeat, a blood pressure sensor element, a temperature sensor element, a pH sensor element or any other types of sensor elements or combinations thereof. The advantages of this disclosure, however, specifically are important for miniaturized analytical sensors, such as miniaturized transcutaneous glucose sensors, having the shape of an elongated strip, e.g., having a length of no more than 20 mm and a width of no more than 3 mm, since, specifically in these miniaturized sensors, the contacting of the electrodes remains a challenge.

The sensor element comprises at least one contact pad, preferably at least two contact pads, more preferably three contact pads. The term "contact pad" as used herein is a broad term and is to be given its ordinary and customary meaning to a person of ordinary skill in the art and is not to be limited to a special or customized meaning. The term specifically may refer, without limitation, to an electrically conductive area or pad that is electrically connected to one of the electrodes of the sensor element and which may be contacted by one or more contacting elements. As an example, the at least one contact pads may comprise one or more metal layers, such as one or more gold layers. Specifically the contact pad may be electrically connected to either the working electrode or the counter electrode or the reference electrode. The contact pad may be located outside of the body of the user. Thus, as an example, the sensor element may comprise at least one implantable or insertable portion configured for insertion into the body tissue and at least one contacting portion configured for remaining outside the body tissue and configured for being contacted by the contact assembly. As an example, in the implantable portion, the sensor element may be or may comprise the shape of a strip having a constant width, whereas, in the contacting portion, the sensor element may be widened in order to provide increased space for placement of the one, two, three or more contact pads. The contact pad may be the area where the sensor element and the contact assembly can be electrically connected.

The term "electrically connected" as used herein is a broad term and is to be given its ordinary and customary meaning to a person of ordinary skill in the art and is not to be limited to a special or customized meaning. The term specifically may refer, without limitation, to a physical state of at least two elements where electrons are able to travel from the one element to the other element when there is an electric voltage applied between the two elements. Specifically two elements are electrically connected when there may be an electric current between the two elements as long as there is a difference in electric potential between the two elements. In particular two electrically conductive elements in physical contact are electrically connected. In the following, the term "electrically contacted" will be used equivalently to the term "electrically connected."

The term "electrically conductive elastomeric element," "electrically conductive elastomer," and "electrically conductive elastomeric material" are used interchangeably herein. These terms are broad and are to be given their ordinary and customary meaning to a person of ordinary skill in the art and are not to be limited to a special or customized meaning. The terms specifically may refer, without limitation, to an arbitrary material or a composition of materials adapted to allow a flow of an electrical current in one or more directions and further adapted to be elastically deformable. In particular, an electrically conductive elastomeric element, electrically conductive elastomer, or electrically conductive elastomeric material may additionally be or may comprise a material which is incompressible. Thus, as an example, the total volume of the electrically conductive elastomeric element may be unchanged in case the electrically conductive elastomeric element is deformed or compressed.

The electrically conductive elastomeric element specifically may comprise at least one electrically conductive rubber, specifically at least one rubber material filled with electrically conductive particles, more specifically filled with one or more of carbon particles or metal particles. Specifically, the electrically conductive rubber may contain a silicone rubber. Other options exist.

As an example, the electrically conductive elastomeric element, electrically conductive elastomer, or electrically conductive elastomeric material may be or may comprise at least one electrically conductive rubber, as will be outlined in further detail below. As an example, the electrically conductive elastomeric element may comprise at least one elastomeric matrix material, with one or more filling materials disposed therein, such as dispersed therein, e.g., one or more of at least one metal powder and/or at least one conductive carbon powder. Additionally or alternatively, the electrically conductive elastomeric element may be or may comprise at least one elastomeric matrix material with one or more electrically conductive fibers, beads or leads disposed therein, such as one or more of fibers, beads or leads made of one or more of metal or conductive carbon. However, different types of electrically conductive rubber may exist. Specifically, the electrically conductive rubber may comprise a non-conductive matrix, such as, for example, silicone and/or rubber, and embedded therein, the electrically conductive rubber may comprise conductive particles, such as, for example, particles comprising one or more of metal or conductive carbon. A grade, ratio or degree of filling may refer to a quantity of particles embedded within the non-conductive matrix. Specifically, the grade of filling with the conductive particles may be such, that the conductive particles electrically contact one another, such as to provide conductive paths through the non-conductive matrix, e.g., through a bulk material. A specific resistance of the electrically conductive rubber comprising the conductive particles embedded within the non-conductive matrix may be, for example, less than 1 Ohm cm. Thus, specifically, the specific resistance of said electrically conductive rubber, e.g., a first type of the electrically conductive rubber, may be quite low. However, other types of the electrically conductive rubber may have a much higher specific resistance, such as for example 100 Ohm cm, or higher. The electrically conductive rubber having such a high specific resistance, e.g., a second type of the electrically conductive rubber, may comprise a conductive matrix, specifically a matrix of inherently conductive rubber, such as, for example, silicon rubber having molecular dispersed carbon. Combinations of different types of electrically conductive rubber however, may also be conceivable. For example, a combination of the first and second type of the electrically conductive rubber, e.g., a third type of the electrically conductive rubber, may comprise conductive particles, specifically metal particles, embedded within the inherently conductive rubber matrix.

The electrically conductive elastomeric element specifically may directly contact the contact pad.

The electrically conductive elastomeric element may have a cylindrical shape. Preferably the electrically conductive elastomeric element may have a circular cylindrical shape, more preferably a roller shape. The contacting between the electrically conductive elastomeric element and the at least one contact pad of the sensor element may take place via one or both of a circumferential surface of the cylinder or a flat front face of the cylinder. Thereof, the contacting via the circumferential surface is specifically advantageous and efficient. Thus, as an example, the electrically conductive elastomeric element may contact the at least one contact pad of the sensor element with a circumferential surface of the electrically conductive elastomeric element.

Further optional embodiments refer to the contact assembly and may also be implemented in the sensor device. Thus, specifically, the first contact pad of the contact assembly may be contacted by a first portion of the electrically conductive elastomeric element. The second contact pad of the contact assembly specifically may be contacted by a second portion of the electrically conductive elastomeric element, wherein the second portion specifically may be different from the first portion. The second portion specifically may change one or both of a position or a shape when the first contact pad exerts the pressure onto the electrically conductive elastomeric element. As an example, both the first portion and the second portion may be circumferential portions on a circumferential surface of the electrically conductive elastomeric element, which, as an example, may be a cylindrical electrically conductive elastomeric element. Additionally or alternatively, however, the first portion may be a portion on a circumferential surface of the electrically conductive elastomeric element, and the second portion may be a front face or a part thereof of the electrically conductive elastomeric element or vice a versa. Specifically, the electrically conductive elastomeric element may have a cylindrical shape, preferably a circular cylindrical shape, more preferably a roller shape, with the cylindrical shape having a front face and a circumferential surface. Therein, the first portion specifically may comprise at least a part of the front face and the second portion specifically may comprise at least a part of the circumferential surface. Additionally or alternatively, however, both the first portion and the second portion may comprise at least a part of the circumferential surface. Other options exist and will be explained in further detail below.

Specifically, the contact assembly may be arranged such that the first contact pad exerts a pressure onto the electrically conductive elastomeric element in a first dimension, thereby compressing the electrically conductive elastomeric element in the first dimension and expanding the electrically conductive elastomeric element in at least one second dimension. By the expansion in the second dimension, the electrically conductive elastomeric element may contact the second contact pad. The first and second dimensions may be directions which are oriented in a nonparallel fashion with respect to one another, such as oriented perpendicular or essentially perpendicular with respect to one another.

Thus, as an example, a cylindrically shaped electrically conductive elastomeric element may be used, with the first dimension being an axial dimension or direction of the cylinder, and the second dimension being a radial dimension or direction of the cylinder, or vice versa. Thus, when compressing the cylinder in a radial dimension, the cylinder may expand in an axial dimension or vice versa. Thus, generally, the elastomeric element may have a cylindrical shape, wherein the first dimension may be an axial direction of the cylindrical shape and wherein the second dimension may be a radial direction of the cylindrical shape. The first contact pad may contact, e.g., a front face of the cylindrical shape and the second contact pad may be contacted by at least a part of a circumferential surface of the cylindrical shape, or vice versa.

Further options refer to the angular relationship between the first and second contact pads. As outlined above, the first and second contact pads are arranged with respect to one another in a nonparallel fashion. Specifically, the first contact pad and the second contact pad may be arranged at an angle of 80° to 100° with respect to one another, specifically at an angle of 90°. As an example, the angle to which reference is made may be an angle between surface normals, such as the smaller angle between the surface normals, of the first and second contact pads. Specifically, the first and second contact pads may be planar contact pads, such as planar rectangular, polygonal, circular, square or oval contact pads.

The contact assembly specifically may further comprise at least one support structure. The at least one electrically conductive elastomeric element may fully or partially be embedded in the support structure. The sensor element specifically may be clamped between at least two clamping elements, wherein at least one of the clamping elements comprises the electrically conductive elastomeric element. The electrically conductive elastomeric element specifically may be clamped between the electronics unit and the support structure, thereby being deformed and exerting a clamping force onto the sensor element. Thus, as outlined above, the second module comprising the electronics unit may, by its own or in interaction with the support structure, compress the electrically conductive elastomeric element, with the second contact pad electrically contacting the electrically conductive elastomeric element, thereby deforming the electrically conductive elastomeric element, wherein, by the deformation, the first contact pad of the sensor element is electrically contacted. The electrically conductive elastomeric element specifically may directly contact the first contact pad.

The support structure may contain at least one mounting hole. Particularly the cylindrically shaped electrically conductive elastomeric element may be partially inserted into the mounting hole, such that the electrically conductive elastomeric element protrudes from the mounting hole.

The term "support structure" as used herein is a broad term and is to be given its ordinary and customary meaning to a person of ordinary skill in the art and is not to be limited to a special or customized meaning. The term specifically may refer, without limitation, to an arbitrary structure adapted to give mechanical stability to at least one other element. Particularly the support structure may limit a deformation, specifically a change of a physical shape, of the other element. Particularly the electrically conductive elastomeric element may be embedded in the support structure.

The term "embedded" as used herein is a broad term and is to be given its ordinary and customary meaning to a person of ordinary skill in the art and is not to be limited to a special or customized meaning. The term specifically may refer, without limitation, to a physical location of a first element with regard to a second element. The first element may be embedded in the second element, when the second element at least partially surrounds and/or encloses the first element in at least one spatial level.

At least one electrically conductive elastomeric element may respectively be provided on opposing sides of the sensor element. Thus at least two electrically conductive elastomeric elements may be arranged, such that the electrically conductive elastomeric elements electrically contact the sensor element from both opposing sides.

The support structure may be fully or partially made of an electrically insulating material. Particularly, the support structure may be made of a technical polymer. Further, the support structure may be fully or partially made of one of the electrically insulating materials selected from the group consisting of: technical polymers; Acrylonitrile butadiene styrene copolymer (ABS); Polycarbonate (PC); modified PC; Polyoxymethylene (POM); Polyether ether ketone (PEEK); Polystyrene (PS); Polypropylene (PP); and Polyethylene terephthalate (PET); Cycloolefin copolymer (COC); ceramics, specifically one or more of $Al_2O_3$, AN or SiC. Further electrically insulating materials are also possible.

Polycarbonate (PC) is available under the trade name Makrolon 2405, for example.

The sensor device may be configured to apply pressure onto the at least one electrically conductive elastomeric element. The pressure may be applied onto the electrically conductive elastomeric element, such that the at least one electrically conductive elastomeric element is deformed by the pressure.

At least two of the clamping elements each comprise at least one electrically conductive elastomeric element, such that the sensor element is clamped in between at least two of the electrically conductive elastomeric elements.

The term "clamping element" as used herein is a broad term and is to be given its ordinary and customary meaning to a person of ordinary skill in the art and is not to be limited to a special or customized meaning. The term specifically may refer, without limitation, to an element adapted to obstruct a spatial movement of at least one other element by a force transmitted by friction. Particularly the clamping element applies pressure onto the other element by physically contacting the other element.

The sensor element may contain contact pads on opposing surfaces. The contact pads on the opposing surfaces of the sensor element each may be electrically contacted by at least one of the electrically conductive elastomeric elements.

The electrically conductive elastomeric element may comprise at least one electrically conductive rubber. Specifically the electrically conductive elastomeric element may comprise at least one rubber material filled with electrically conductive particles. More specifically the electrically conductive elastomeric element may comprise at least one rubber material filled with one or more of carbon particles or metal particles. Further, the electrically conductive rubber may comprise a silicone rubber.

The sensor element, as outlined above, specifically may be clamped between at least two clamping elements, wherein at least one of the clamping elements comprises the electrically conductive elastomeric element. Thus, as an example, the sensor element may be clamped between an electrically conductive elastomeric element and at least one further clamping element other than the electrically conductive elastomeric element. Additionally or alternatively, the sensor element may be clamped between at least two electrically conductive elastomeric elements and at least one further clamping element other than an electrically conductive elastomeric element. Alternatively, the sensor element may be clamped in between two electrically conductive elastomeric elements or in between two electrically conductive elastomeric elements on one side of the sensor element and at least one further electrically conductive elastomeric element on an opposing side of the sensor element. Thus, as an example, the sensor element may be contacted, on a first side, by two electrically conductive elastomeric elements. The sensor element further may be contacted, on a second side opposing the first side, by at least one electrically conductive elastomeric element.

The sensor element, on a first side, may be contacted by two electrically conductive elastomeric elements. On a second side of the sensor element opposing the first side, the sensor element may be contacted by at least one electrically conductive elastomeric element.

The at least two clamping elements may also function as contacting elements for electrically contacting the at least one contact pad. Thus, as an example, one of the clamping elements may be or may comprise the at least one electrically conductive elastomeric element functioning as a contacting element for electrically contacting at least one contact pads on a first side of the sensor element. The at least one further clamping element, specifically on an opposing, second side of the sensor element, may be or may comprise at least one further contacting element which may also comprise at least one electrically conductive elastomeric element and/or at least one other contacting element, for electrically contacting at least one contact pad on the second, opposing side of the sensor element. Alternatively, however, all contact pads may be on one and the same side of the sensor element, such as on the above-mentioned first side or second side, and at least one contacting element may be provided on this side, only, whereas, on the opposing side, at least one clamping element may be provided without electrical contacting function, for mere mechanical stabilization and clamping. Thus, the contact assembly may comprise a plurality of electrically conductive elastomeric elements provided on opposing sides of the sensor element, electrically contacting the sensor element from both opposing sides. The sensor element, on a first side, may be contacted by two electrically conductive elastomeric elements. Further, the sensor element, on a second side opposing the first side, may be contacted by the at least one electrically conductive elastomeric element or by at least one of a plurality of the electrically conductive elastomeric elements.

The electrically conductive elastomeric element may be incompressible or may have a low compressibility. Thus, specifically, when exerting a pressure onto the electrically conductive elastomeric element in one direction or dimension, thereby compressing the electrically conductive elastomeric element in one direction, the electrically conductive elastomeric element may expand in at least one other direction or dimension, thereby maintaining an essentially constant volume. Particularly the electrically conductive elastomeric element may have a Poisson's ratio ν of 0.3 to 0.7, preferably of 0.4 to 0.6, more preferably of 0.5. The term "Poisson's ratio" as used herein is a broad term and is to be given its ordinary and customary meaning to a person of ordinary skill in the art and is not to be limited to a special or customized meaning. The term specifically may refer, without limitation, to a material property, particularly to a ratio of stretching and compressing along an arbitrarily chosen axis of a material. The Poisson's ratio can be determined by $$\nu = -(d\varepsilon\_\text{trans}/d\varepsilon\_\text{axial}),$$

wherein ν is the Poisson's ratio, ε_trans is the transverse strain, particularly transverse to the chosen axis, and ε_axial is the axial strain, particularly in the direction of the chosen axis.

A first spatial extent of a geometric form of the electrically conductive elastomeric element may be 1 to 10 times as long as a second spatial extent of the geometric form of the electrically conductive elastomeric element, when no pressure is applied onto the electrically conductive elastomeric element. Preferably the first spatial extent of the geometric form of the electrically conductive elastomeric element may be 2 to 5, more preferably 2 to 3, times as long as the second spatial extent of the geometric form of the electrically conductive elastomeric element.

The sensor device comprises the at least one electronics unit. The term "electronics unit" as used herein is a broad term and is to be given its ordinary and customary meaning to a person of ordinary skill in the art and is not to be limited to a special or customized meaning ("electronics unit" may also be used interchangeably herein with "electronics" or "electronics assembly"). The term specifically may refer, without limitation, to an arbitrary component which is designed to actuate an arbitrary sensor and/or to record signals from the sensor and/or to derive at least one item of information of the at least one analyte from the signals and/or to evaluate these signals in whole or part. The electronics unit, as an example, may comprise at least one transmitter for transmitting data, such as measurement data obtained by using the at least one sensor element. The transmission may take place, as an example, to at least one evaluation device and/or at least one data management device. The at least one electronics unit, as an example, may further comprise at least one voltage measurement device and/or at least one current measurement device, e.g., for performing one or more of the above-mentioned analyte measurements using the electrochemical sensor element. Thus, as an example, the at least one voltage measurement device and/or the at least one current measurement device may be configured for performing at least one amperometric and/or at least one potentiostatic measurement. The electronics unit may be configured for one or more of performing at least one analyte measurement by using the sensor element, storing measurement data or transmitting measurement data.

The electronics unit specifically may comprise at least one printed circuit board (PCB). The second contact pad may be comprised by the printed circuit board, e.g., by being located on one or both sides of the printed circuit board. Specifically, the printed circuit board may be a rigid printed circuit board, with the at least one second contact pad being located on one or both sides of the printed circuit board.

The term "printed circuit board" as used herein is a broad term and is to be given its ordinary and customary meaning to a person of ordinary skill in the art and is not to be limited to a special or customized meaning. The term specifically may refer, without limitation, to an element which is configured for mechanically supporting and electrically connecting one or more electronic components. The printed circuit board, specifically, may be or may comprise at least one planar element, such as a board or a plate, e.g., a board or a plate made of one or more of a plastic material such as a resin like, e.g., FR-4 glass epoxy, a ceramic material, a cardboard material or a metal. The board or plate may have, on one or both sides, one or more electrical traces, wherein at least one of the electrical traces may contact the second contact pad. The at least one second contact pads may be located on one or both of the surfaces of the printed circuit board. Further, the printed circuit board may carry one or more electronics components, such as one or more active or passive components. As an example, the printed circuit board may carry and/or comprise one or more processors and/or integrated circuits, such as one or more application-specific integrated circuits (ASICs). As an example, the at least one printed circuit board may carry and/or comprise one or more components such as components selected from the group consisting of capacitors, resistors or active devices. The one or more components may be located on at least one surface of the printed circuit board or, additionally or alternatively, may also fully or partially be embedded into the printed circuit board, such as into a substrate of the printed circuit board.

As an example, the first and/or the second module, specifically the first and/or the second component, may comprise at least one molded interconnect device (MID), specifically a MID-part. The contact pads may for example be inherent parts of the support structure. Particularly, the MID may be or may comprise a plastic part, preferably a plastic part partially metallized in order to provide conductive paths and/or areas. The MID may specifically be arranged for replacing for example a circuit board, specifically the printed circuit board.

The sensor device may further comprise at least one housing patch, also referred to as a body mount, configured for being mounted onto the skin of the user, wherein the housing patch is configured for receiving the electronics unit.

The contact assembly may be fully comprised in the housing patch, such that the sensor element may be mounted to the housing patch and is electrically contacted by the housing patch, with or without the electronics unit being present. For mounting to the skin of the user, the housing patch may comprise one or more mounting elements, such as one or more adhesive surfaces, e.g., by providing one or more adhesive strips or plasters.

The housing patch, as an example, may comprise a base plate having an opening therein, through which the sensor element extends into the body tissue. Therein, as an example, the sensor element may be a flat sensor element, wherein a substrate of the flat sensor element extends in one plane. This plane, as an example, may be located in a nonparallel fashion with respect to the base plate. As an example, the plane of the sensor element may be oriented at essentially 90° with respect to a plane of the base plate, e.g., with a deviation from 90° of no more than 20°, preferably of no more than 10° or no more than 5°. Thus, as an example, the sensor element may be a flat sensor element, having a hockey stick shape, with a contacting portion and an insertable portion which are oriented in an angled fashion with respect to one another. The contact assembly, as an example, may comprise two, three or more electrically conductive elastomeric elements as clamping elements, which are shaped as pins or cylinders, and which, as an example, protrude directly or indirectly from the base plate, e.g., at an angle of essentially 90°. The contacting portion of the sensor element, which may be oriented essentially perpendicular with respect to the base plate, may be inserted in between the pins or cylinders. In this arrangement, the insertion of a sensor element into the housing patch is specifically simple, since the insertable portion simply has to be pushed through the opening of the base plate and the contacting portion simply has to be pushed in between the pins or cylinders formed by the electrically conductive elastomeric elements. Consequently, no tool or complicated mechanical aid is required for electrically contacting the sensor element. The insertion of the sensor element and the electrical contacting specifically may be performed in an automatic fashion, since the pins or cylinders may be freely accessible from above.

The electronics unit further may be configured for being mated to the housing patch. Specifically the electronics unit may be configured for being releasably mated to the housing patch.

The sensor device may be configured for exerting a pressure onto the at least one electrically conductive elastomeric element. The sensor device may further be configured to maintain the pressure when the sensor device is mated to the electronics unit.

The electronics unit may have at least one contact area. The term "contact area" as used herein is a broad term and is to be given its ordinary and customary meaning to a person of ordinary skill in the art and is not to be limited to a special or customized meaning. The term specifically may refer, without limitation, to an area that allows electrically connecting the electronics unit. Specifically the contact area may be configured to allow a passing of electrical signals from and to the electronics unit. The contact area, as an example, may be provided by providing one or more electrically conductive paths, such as one or more metal pads, or by providing one or more contact elements, such as one or more electrically conductive spring contacts or the like.

The electrically conductive elastomeric element may be configured for electrically contacting both the sensor element and the contact area. Thus, the electrically conductive elastomeric element may be located and embodied to directly provide an electrical connection in between the contact pad of the sensor element and the contact area of the electronics unit.

Further the at least one electrically conductive elastomeric element may, with at least one first section, electrically contact the sensor element and, with at least one second section, electrically contact the contact area of the electronics unit.

The contact assembly may be configured to deform the electrically conductive elastomeric element by pressing the sensor element into the electrically conductive elastomeric element. The first section may be a deformed section and the second section may be a non-deformed section.

At least one of the clamping elements may be part of the electronics unit. Thus, as an example, the housing patch without the electronics unit may provide those clamping elements, wherein one or both of the clamping elements contain the at least one electrically conductive elastomeric element. Alternatively, however, at least one of the clamping elements may be provided by the housing patch, whereas at least another one of the clamping elements may be provided by the electronics unit, such that the clamping and electrical contacting of the sensor element is effected when the electronics unit is clamped or mounted onto the housing patch, including the electrical contacting of the sensor element.

In a further aspect, a medical device for detecting at least one analyte in a body fluid of a user is disclosed. The medical device comprises the sensor device according to any one of the embodiments as described above or as described in further detail below and at least one insertion needle for transcutaneously inserting the sensor element, specifically at least one implantable portion of the sensor element, into the body tissue.

Further the sensor element may be at least partially received in the insertion needle.

This disclosure further refers to a method for electrically interconnecting at least two modules, specifically by using the contact assembly according to any one of the preceding embodiments referring to a contact assembly or according to any one of the embodiments described in further detail below. The method comprises the following steps. The method steps may be performed in the given order. However, other orders of the method steps are feasible. Further, one or more of the method steps may be performed in parallel and/or on a timely overlapping fashion. Further, one or more of the method steps may be performed repeatedly. Further, additional method steps may be present which are not listed.

Method comprises the following method steps:
i. providing at least one first module having at least one first contact pad;
ii. providing at least one second module having at least one second contact pad;
iii. providing at least one electrically conductive elastomeric element; and
iv. arranging the first and second modules and the electrically conductive elastomeric element such that one of the first contact pad or the second contact pad exerts a pressure onto the electrically conductive elastomeric element, thereby deforming the electrically conductive elastomeric element, wherein, by the deformation, the other one of the first contact pad or the second contact pad is contacted by the electrically conductive elastomeric element.

The method may fully or partially be performed by hand or may fully or partially be embodied in an automated fashion, such as fully automatically.

The method specifically may be performed such that, in step iv., the first and second modules and the electrically conductive elastomeric element are arranged such that the first contact pad and the second contact pad are arranged in a nonparallel fashion with respect to one another.

Further disclosed is a method for manufacturing a sensor device for detecting at least one analyte in a body fluid of a user, specifically a sensor device according to any one of the embodiments described above or as described in further detail below. The method comprises the method steps as listed as follows. The method steps may be performed in the given order. However, other orders of the method steps are feasible. Further, one or more of the method steps may be performed in parallel and/or on a timely overlapping fashion. Further, one or more of the method steps may be performed repeatedly. Further, additional method steps may be present which are not listed.

The method comprises the following steps:
a) providing at least one sensor element for electrochemically detecting the at least one analyte, the sensor element having at least one contact pad;
b) providing at least one electronics unit, wherein the electronics unit comprises at least one second contact pad; and
c) electrically interconnecting the first contact pad of the sensor element and the second contact pad of the electronics unit by using the method for electrically interconnecting at least two modules as described above, wherein the sensor element is used as the first module and wherein the electronics unit is used as the second module.

Specifically, the method may comprise using the sensor device as described above or as will further be described below.

The sensor device further may comprise at least one housing patch configured for being mounted on-to the skin of the user. The housing patch may be configured for receiving the electronics unit. Step c) may be performed when mounting the electronics unit to the housing patch.

Positioning the sensor element relative to the sensor device such that a physical contact between the contact pad of the sensor element and the electrically conductive elastomeric element of the sensor device is established, may be performed as an additional step between step b) and step c).

The proposed methods and devices provide many advantages over known devices and methods. Commonly, in order to allow electrically connecting at least two electrical structures, such as a contact pad and/or a contact area, with each other, a first electrical structure is positioned in the same plane to a second electrical structure. Alternatively the first electrical structure can be arranged parallel to the second electrical structure, such that their surfaces are facing each other. On the other hand, an electrical connection between at least two electrical structures may be established when they are arranged perpendicularly. Specifically, it may be possible to electrically connect a sensor element and an electronics unit, when the electrical structure of the sensor element, particularly a contact pad, is arranged vertically on the electrical structure of the electronics unit, particularly a contact area.

Summarizing and without excluding further possible embodiments, the following embodiments may be envisaged:

Embodiment 1

A contact assembly for electrically interconnecting at least two modules, the contact assembly having at least one first contact pad comprised by a first one of the modules and at least one second contact pad comprised by a second one of the modules, wherein the contact assembly further comprises at least one electrically conductive elastomeric element, wherein the contact assembly is arranged such that one of the first contact pad or the second contact pad exerts a pressure onto the electrically conductive elastomeric element, thereby deforming the electrically conductive elastomeric element, wherein, by the deformation, the other one of the first contact pad or the second contact pad is contacted by the electrically conductive elastomeric element.

Embodiment 2

The contact assembly according to the preceding embodiment, wherein the first contact pad and the second contact pad are arranged in a nonparallel fashion with respect to one another.

Embodiment 3

The contact assembly according to any one of the preceding embodiments, wherein the first one of the modules comprises at least one sensor element for detecting at least one analyte.

Embodiment 4

The contact assembly according to any one of the preceding embodiments, wherein the first contact pad is contacted by a first portion of the electrically conductive elastomeric element and wherein the second contact pad is contacted by a second portion of the electrically conductive elastomeric element, wherein the second portion changes one or both of a position or a shape when the first contact pad exerts the pressure onto the electrically conductive elastomeric element.

Embodiment 5

The contact assembly according to the preceding embodiment, wherein the electrically conductive elastomeric element has a cylindrical shape, preferably a circular cylindrical shape, more preferably a roller shape, with the cylindrical shape having a front face and a circumferential surface.

Embodiment 6

The contact assembly according to the preceding embodiments, wherein the first portion comprises at least a part of the front face and wherein the second portion comprises at least a part of the circumferential surface.

Embodiment 7

The contact assembly according to any one of the three preceding embodiments, wherein both the first portion and the second portion comprise at least a part of the circumferential surface.

Embodiment 8

The contact assembly according to any one of the preceding embodiments, wherein the first contact pad and the second contact pad are arranged at an angle of 80° to 100° with respect to one another, specifically at an angle of 90°.

Embodiment 9

The contact assembly according to any one of the preceding embodiments, wherein the contact assembly is arranged such that the first contact pad exerts a pressure onto the electrically conductive elastomeric element in a first dimension, thereby compressing the electrically conductive elastomeric element in the first dimension and expanding the electrically conductive elastomeric element in at least one second dimension, whereby the electrically conductive elastomeric element contacts the second contact pad.

Embodiment 10

The contact assembly according to the preceding embodiment, wherein the electrically conductive elastomeric element has a cylindrical shape, wherein the first dimension is an axial direction of the cylindrical shape, wherein the second dimension is a radial direction of the cylindrical shape, wherein the first contact pad contacts a front face of the cylindrical shape and wherein the second contact pad is contacted by at least a part of a circumferential surface of the cylindrical shape.

Embodiment 11

The contact assembly according to any one of the preceding embodiments, wherein the electrically conductive elastomeric element comprises at least one electrically conductive rubber, specifically at least one rubber material filled with electrically conductive particles, more specifically filled with one or more of carbon particles or metal particles.

Embodiment 12

The contact assembly according to any one of the preceding embodiments, wherein the electrically conductive rubber contains a silicone rubber.

Embodiment 13

A sensor device for detecting at least one analyte in a body fluid of a user, the sensor device comprising the contact assembly according to any one of the preceding embodiments:
  wherein the first module of the contact assembly comprises at least one sensor element for electrochemically detecting the at least one analyte, the sensor element having the at least one first contact pad of the contact assembly; and
  wherein the second module of the contact assembly comprises at least one electronics unit (138), wherein the electronics unit (138) comprises the at least one second contact pad of the contact assembly.

Embodiment 14

The sensor device according to the preceding embodiment, wherein the contact assembly further comprises at least one support structure, wherein the at least one electrically conductive elastomeric element is fully or partially embedded in the support structure, wherein the sensor element is clamped between at least two clamping elements, wherein at least one of the clamping elements comprises the electrically conductive elastomeric element.

Embodiment 15

The sensor device according to the preceding embodiment, wherein the electrically conductive elastomeric element is clamped between the electronics unit and the support structure, thereby being deformed and exerting a clamping force onto the sensor element.

Embodiment 16

The sensor device according to any one of the preceding embodiments referring to a sensor device, wherein the electrically conductive elastomeric element directly contacts the contact pad.

Embodiment 17

The sensor device according to any one of the preceding embodiments referring to a sensor device, wherein the electrically conductive elastomeric element has a cylindrical shape, preferably a circular cylindrical shape, more preferably a roller shape.

Embodiment 18

The sensor device according to the preceding embodiment, wherein the at least one electrically conductive elastomeric element contacts the at least one contact pad of the sensor element with a circumferential surface of the electrically conductive elastomeric element.

Embodiment 19

The sensor device according to any one of the two preceding embodiments, wherein the support structure contains at least one mounting hole, wherein the cylindrically-shaped electrically conductive elastomeric element is partially inserted into the mounting hole, such that the electrically conductive elastomeric element protrudes from the mounting hole.

Embodiment 20

The sensor device according to any one of the preceding embodiments referring to a sensor device, wherein electrically conductive elastomeric elements are provided on opposing sides of the sensor element, electrically contacting the sensor element from both opposing sides.

Embodiment 21

The sensor device according to any one of the preceding embodiments referring to a sensor device, wherein the support structure is fully or partially made of an electrically insulating material.

Embodiment 22

The sensor device according to any one of the preceding embodiments referring to a sensor device, wherein the support structure is fully or partially made of one of the electrically insulating materials selected from the group consisting of: technical polymers; Acrylonitrile butadiene styrene copolymer (ABS); Polycarbonate (PC); modified PC; Polyoxymethylene (POM); Polyether ether ketone (PEEK); Polystyrene (PS); Polypropylene (PP); and Polyethylene terephthalate (PET); Cycloolefin copolymer (COC); ceramics, specifically one or more of $Al_2O_3$, AlN or SiC.

Embodiment 23

The sensor device according to any one of the preceding embodiments referring to a sensor device, wherein the sensor device is configured to apply pressure onto the at least one electrically conductive elastomeric element, wherein the at least one electrically conductive elastomeric element is deformed by the pressure.

Embodiment 24

The sensor device according to any one of the preceding embodiments referring to a sensor device, wherein at least two of the clamping elements each comprise at least one electrically conductive elastomeric element, such that the sensor element is clamped in between at least two of the electrically conductive elastomeric elements.

Embodiment 25

The sensor device according to the preceding embodiment, wherein the sensor element contains contact pads on opposing surfaces, wherein the contact pads on the opposing surfaces each are electrically contacted by at least one of the electrically conductive elastomeric elements.

Embodiment 26

The sensor device according to any one of the preceding embodiments referring to a sensor device, wherein the electrically conductive elastomeric element comprises at least one electrically conductive rubber, specifically at least one rubber material filled with electrically conductive particles, more specifically filled with one or more of carbon particles or metal particles.

Embodiment 27

The sensor device according to the preceding embodiment, wherein the electrically conductive rubber contains a silicone rubber.

Embodiment 28

The sensor device according to any one of the two preceding embodiments, wherein the sensor element, on a first side, is contacted by two electrically conductive elastomeric elements and wherein the sensor element, on a second side opposing the first side, is contacted by at least one electrically conductive elastomeric element.

Embodiment 29

The sensor device according to any one of the preceding embodiments referring to a sensor device, wherein the at least one electrically conductive elastomeric element has a Poisson's ratio v of 0.3 to 0.7, preferably of 0.4 to 0.6, more preferably of 0.5.

Embodiment 30

The sensor device according to any one of the preceding embodiments, wherein when no pressure is applied to the at least one electrically conductive elastomeric element, a first spatial extent of a geometric form of the electrically conductive elastomeric element is 1 to 10, preferably 2 to 5, more preferably 2 to 3, times as long as a second spatial extent of the geometric form of the electrically conductive elastomeric element.

Embodiment 31

The sensor device according to any one of the preceding embodiments referring to a sensor device, wherein the electronics unit is configured for one or more of performing at least one analyte measurement by using the sensor element, storing measurement data or transmitting measurement data.

Embodiment 32

The sensor device according to any one of the preceding embodiments referring to a sensor device, wherein the sensor device comprises at least one housing patch configured for being mounted onto the skin of the user, wherein the housing patch is configured for receiving the electronics unit.

Embodiment 33

The sensor device according to the preceding embodiment, wherein the contact assembly is fully comprised in the housing patch, such that the sensor element may be mounted to the housing patch and is electrically contacted by the housing patch, with or without the electronics unit being present.

Embodiment 34

The sensor device according to any one of the two preceding embodiments, wherein the electronics unit is configured for being mated to the housing patch, specifically releasably.

Embodiment 35

The sensor device according to the preceding embodiment, wherein the sensor device is configured for exerting a pressure onto the at least one electrically conductive elastomeric element, and wherein the sensor device is configured to maintain the pressure when the sensor device is mated to the electronics unit.

Embodiment 36

The sensor device according to any one of the six preceding embodiments, wherein the electronics unit has at least one contact area.

Embodiment 37

The sensor device according to the preceding embodiment, wherein the electrically conductive elastomeric element is configured for electrically contacting both the sensor element and the contact area.

Embodiment 38

The sensor device according to the preceding embodiment, wherein the at least one electrically conductive elastomeric element, with at least one first section, electrically contact the sensor element and, with at least one second section, electrically contacts the contact area of the electronics unit.

Embodiment 39

The sensor device according to the preceding embodiment, wherein the contact assembly is configured to deform the electrically conductive elastomeric element by pressing the sensor element into the electrically conductive elastomeric element, wherein the first section is a deformed section and wherein the second section is a non-deformed section.

Embodiment 40

The sensor device according to any one of the ten preceding embodiments, wherein at least one of the clamping elements is part of the electronics unit.

Embodiment 41

A medical device for detecting at least one analyte in a body fluid of a user, comprising the sensor device according to any one of the preceding embodiments referring to a sensor device and further comprising at least one insertion needle for transcutaneously inserting the sensor element, specifically at least one implantable portion of the sensor element, into the body tissue.

Embodiment 42

The medical device according to the preceding embodiment, wherein the sensor element is at least partially received in the insertion needle.

Embodiment 43

A method for electrically interconnecting at least two modules, specifically by using the contact assembly according to any one of the preceding embodiments referring to a contact assembly, the method comprising:
  i. providing at least one first module having at least one first contact pad;
  ii. providing at least one second module having at least one second contact pad;
  iii. providing at least one electrically conductive elastomeric element; and iv. arranging the first and second modules and the electrically conductive elastomeric element such that one of the first contact pad or the second contact pad exerts a pressure onto the electrically conductive elastomeric element, thereby deforming the electrically conductive elastomeric element, wherein, by the deformation, the other one of the first contact pad or the second contact pad is contacted by the electrically conductive elastomeric element.

Embodiment 44

The method according to the preceding embodiment, wherein, in step iv., the first and second modules and the electrically conductive elastomeric element are arranged such that the first contact pad and the second contact pad are arranged in a nonparallel fashion with respect to one another.

BRIEF DESCRIPTION OF THE DRAWINGS

The above-mentioned aspects of exemplary embodiments will become more apparent and will be better understood by reference to the following description of the embodiments taken in conjunction with the accompanying drawings, wherein.

DESCRIPTION

The embodiments described below are not intended to be exhaustive or to limit the invention to the precise forms disclosed in the following detailed description. Rather, the embodiments are chosen and described so that others skilled in the art may appreciate and understand the principles and practices of this disclosure.

Figure 1:
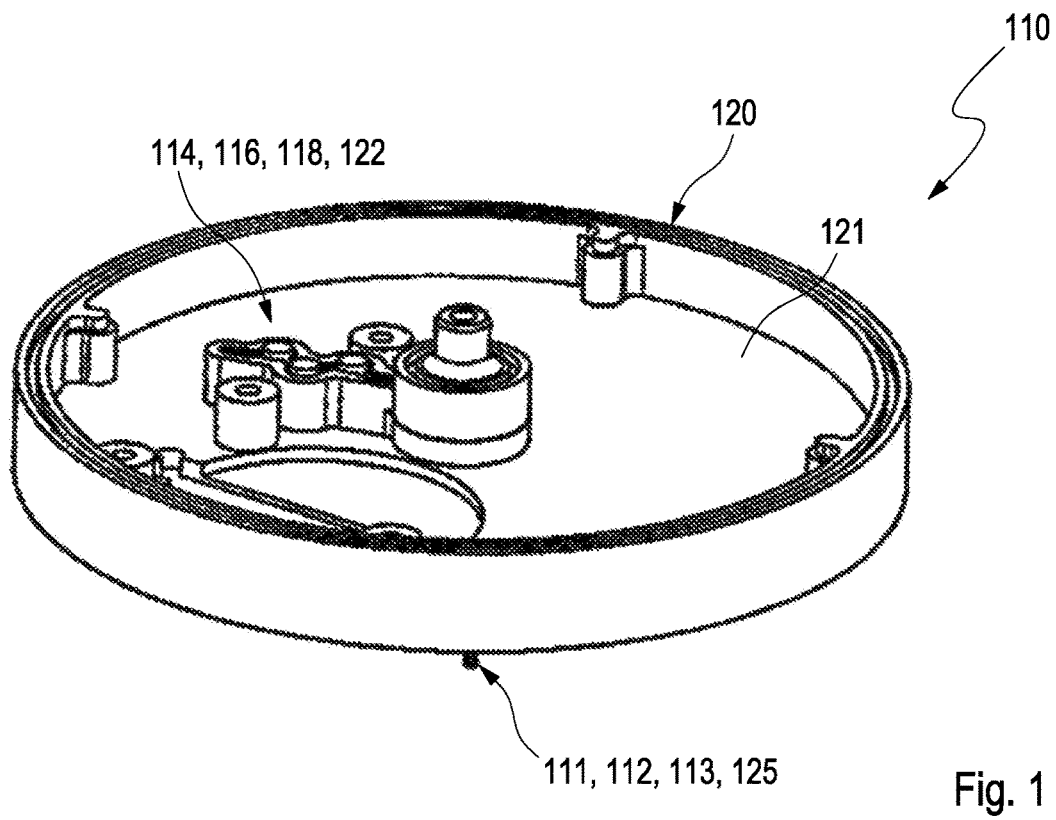
FIG. 1 shows a perspective view of a first embodiment of a contact assembly in a sensor device for detecting at least one analyte in a body fluid of a user.
Figure 6:
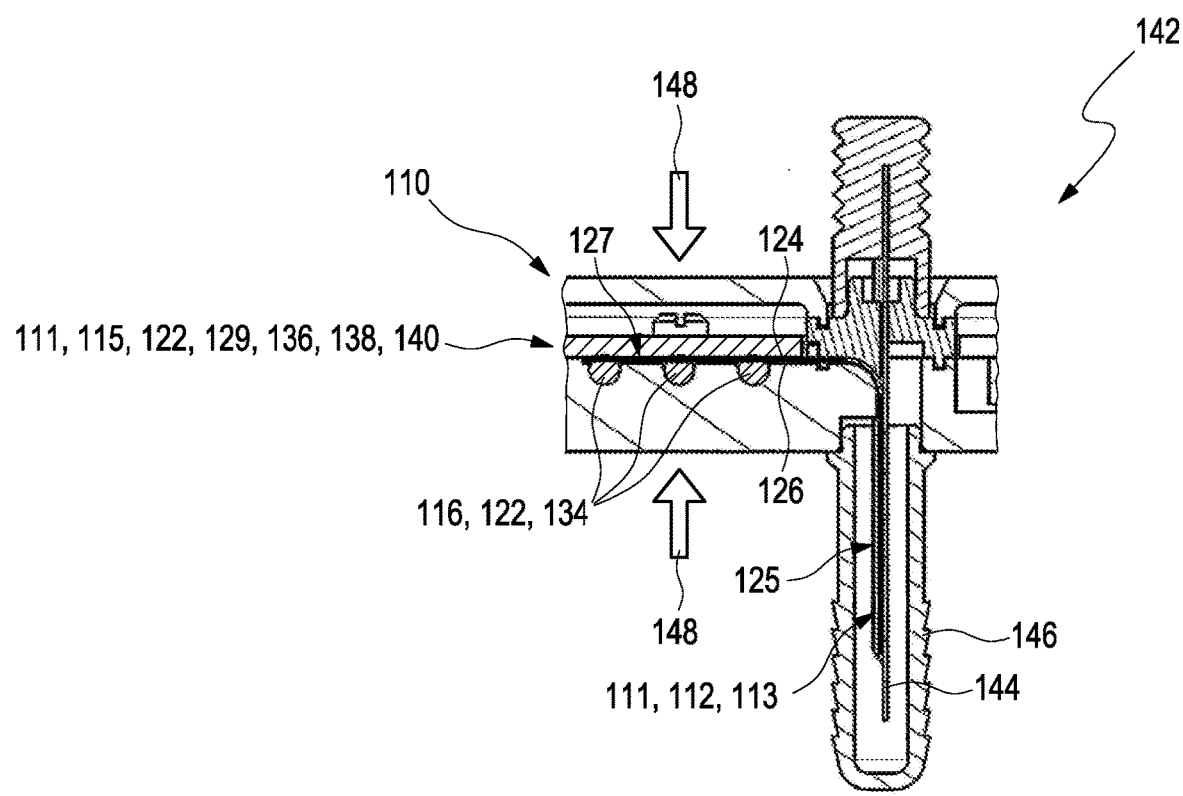
FIG. 6 shows a cross-sectional view of a medical device for detecting at least one analyte in a body fluid of a user.
Figure 7:
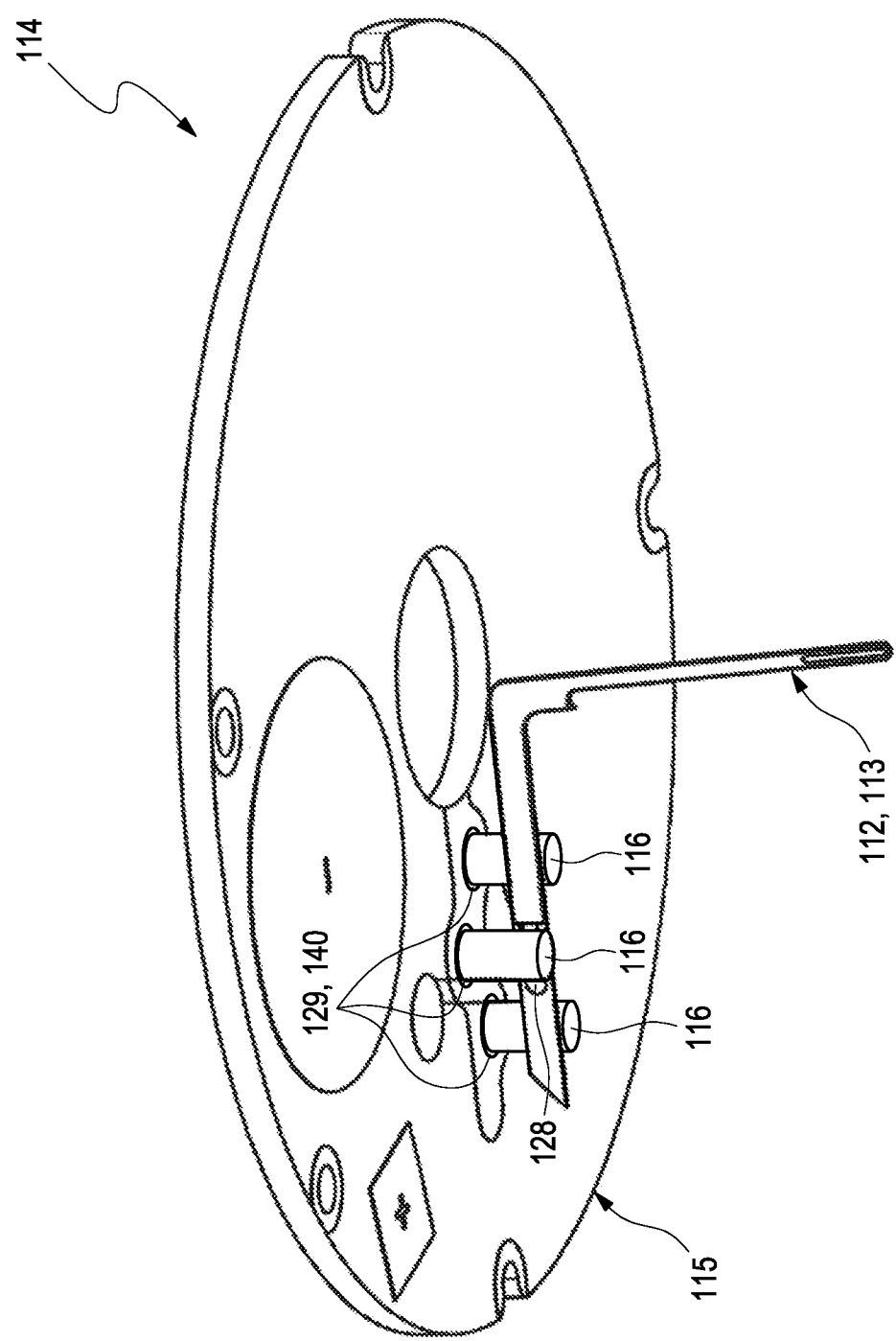
FIG. 7 shows a perspective view of an embodiment of a contact assembly interconnecting a first module and a second module.

In FIG. 1, a first embodiment of a sensor device 110 for detecting at least one analyte in a body fluid of a user is illustrated in a perspective view. The sensor device 110 comprises a contact assembly 114 for electrically interconnecting at least two modules 111. A first module 113 comprises a sensor element 112 for electrochemically detecting the analyte. The second module 115, as illustrated in FIG. 6 and FIG. 7, comprises an electronics unit 138. The contact assembly 114 as illustrated in FIG. 1 comprises three electrically conductive elastomeric elements 116, which each form a clamping element 122, and a support structure 118. The sensor device 110 further comprises a housing patch 120, which may be configured for being mounted onto a skin of a user.

Figure 2:
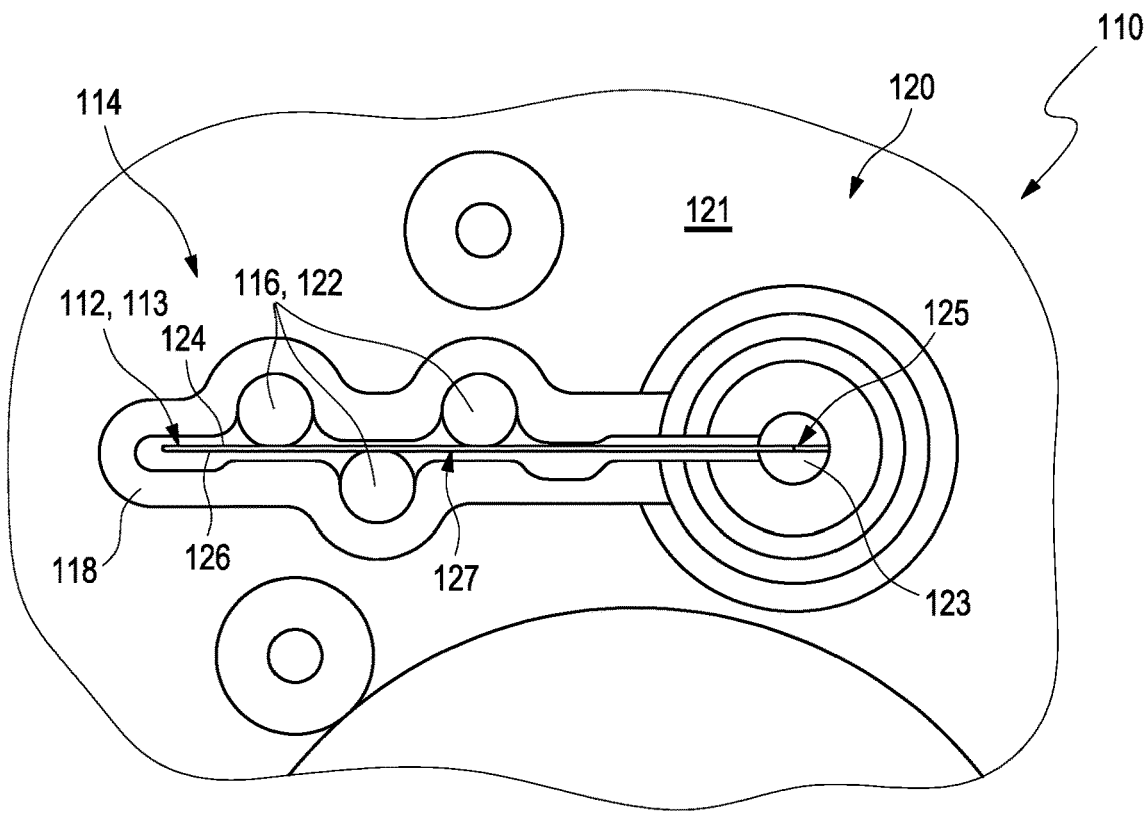
FIG. 2 shows a section of a top plan view of the first embodiment of a contact assembly in a sensor device.

FIG. 2 shows a section of a top plan view of the first embodiment of a sensor device 110 with the contact assembly 114 as shown in FIG. 1. As can be seen, the three electrically conductive elastomeric elements 116 are partially embedded in the support structure 118. The first module 113, specifically the sensor element 112, is clamped between three clamping elements 122. In FIG. 2 each of the three clamping elements 122 comprises one of the electrically conductive elastomeric elements 116 and preferably consists of one of the electrically conductive elastomeric elements 116. The electrically conductive elastomeric elements 116 are arranged on two opposing sides of the sensor element 112, such that the sensor element 112 is clamped between the electrically conductive elements 116. Two electrically conductive elastomeric elements 116 are arranged on a first side 124 of the sensor element 112 and one electrically conductive elastomeric element 116 is arranged on a second side 126 of the sensor element 112. The electrically conductive elastomeric elements 116 each may be pin-shaped and may protrude from a base plate 121 of the housing patch 120 in an essentially perpendicular fashion. The base plate 121 may comprise an opening 123, visible in FIG. 2, through which an insertable portion 125 of the sensor element 112 may extend. A contacting portion 127 of the sensor element 112 is clamped from above in between the pin-shaped electrically conductive elastomeric elements 116. Thus clamping from above allows for an easy insertion of the sensor element 112 which avoids moving parts and which may easily be accomplished by a machine or tool such as an inserter. This clamping from above specifically may be done by the contact surfaces of a printed circuit board (PCB) (not shown in the figures) comprised by the electronics unit 138, which may be mounted on top of the arrangement and forced down towards the conductive elastomeric elements 116.

The support structure 118 may at least partially surround the three electrically conductive elastomeric elements 116 and the sensor element 112, as can be seen in FIG. 2. Thus the support structure 118 may give mechanical stability to the electrically conductive elastomeric elements 116 and the sensor element 112.

Figure 3:
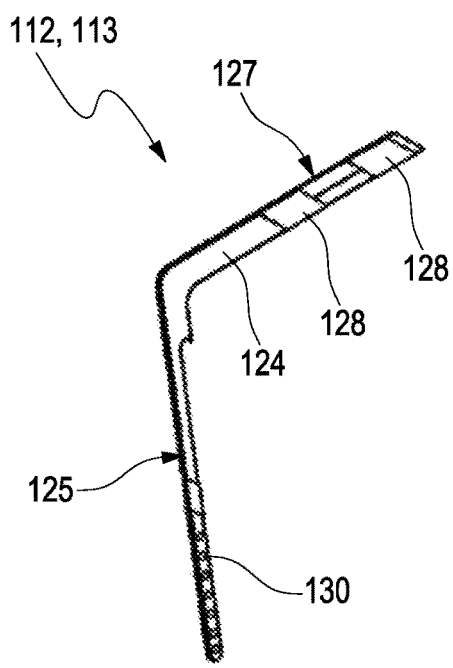
FIGS. 3A and 3B show an embodiment of a sensor element of the first embodiment of a sensor device, in a rear view (FIG. 3A) and in a front view (FIG. 3B)
Figure 3:
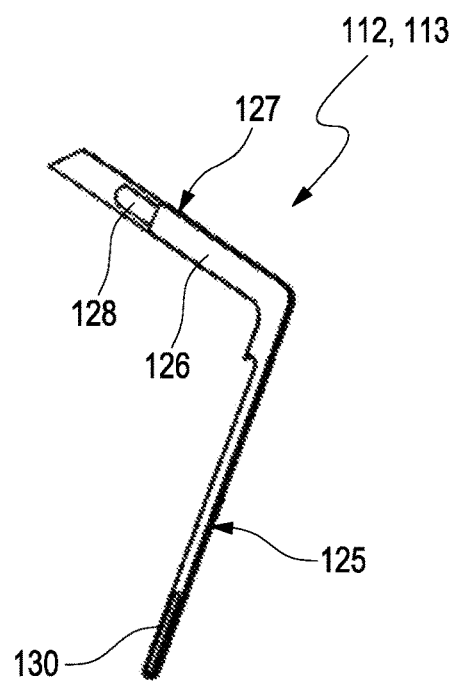

The FIGS. 3A and 3B show one embodiment of the sensor element 112, specifically the sensor element 112 as shown in FIG. 1 and FIG. 2, comprised by the first module 113. In FIG. 3A a rear view of the sensor element 112 is shown, where the first side 124 of the sensor element 112 is in plain sight. In FIG. 3B a front view of the sensor element 112 can be seen, where the second side 126 of the sensor element 112 is in plain sight. As can be seen, the sensor element 112 is basically flat, extending in a single plane which, according to the setup of the FIGS. 1 and 2, may be oriented essentially perpendicular to the plane of the base plate 121. The sensor element 112, specifically, may have the shape of a hockey stick, with the contacting portion 127 and the insertable portion 125 being oriented at an angle. The contacting portion 127 may be widened as compared to the insertable portion 125. Thus, by widening the contacting portion 127, an increased area for electrical contacting is provided and, further, the mechanical stability is increased which is advantageous for the insertion of the contacting portion 127 in between the pin-shaped electrically conductive elastomeric elements 116.

The sensor element 112 may comprise three first contact pads 128. Specifically, the sensor element 112 may comprise two first contact pads 128 on the first side 124 and one first contact pad 128 on the second side 126 of the sensor element 112. The first contact pads 128 may differ in shape and size. As can be seen in FIGS. 3A and 3B, the first contact pads 128 on the first side 124 of the sensor element 112 may have a rectangular shape, while the first contact pad 128 on the second side 126 of the sensor element 112 may have a more rounded shape and be slightly smaller than the other first contact pads 128. Other shapes and sizes of the first contact pads 128, which are not shown in the Figures, are also possible. The sensor element 112 may further comprise at least two, preferably more than two, electrodes 130. The electrodes 130 may be electrically connected to the first contact pads 128. Different forms of electrodes 130 are possible. Specifically at least one of the electrodes 130 may be a working electrode and/or a counter electrode and/or a reference electrode.

Figure 4:
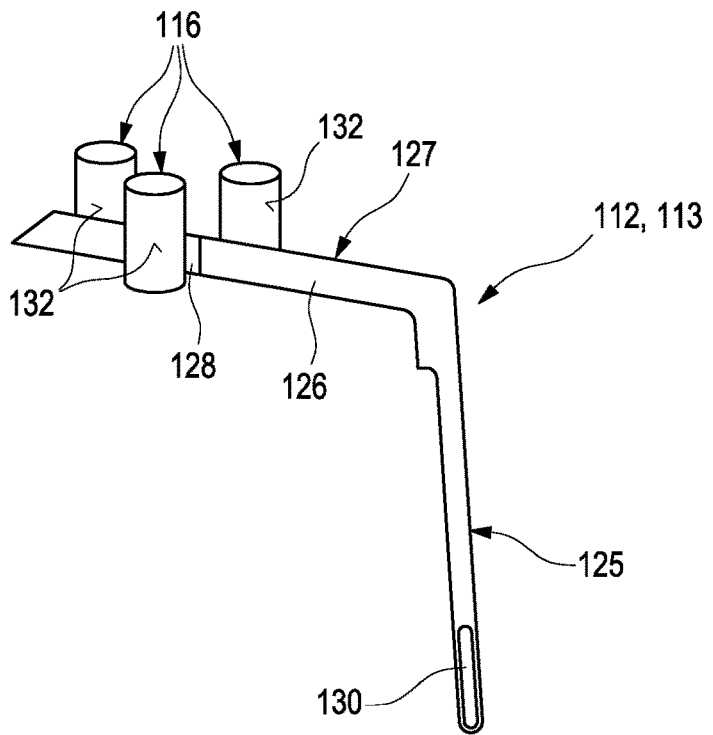
FIG. 4 shows an embodiment of a sensor element and a first part of a contact assembly, in a perspective view.

FIG. 4 shows the first module 113, e.g., the sensor element 112, and the three electrically conductive elastomeric elements 116. In this embodiment, the electrically conductive elastomeric elements 116 are arranged, such that each electrically conductive elastomeric element 116 directly contacts one of the first contact pads 128 of the sensor element 112. The electrically conductive elastomeric elements 116 may have a cylindrical shape, preferably a circular cylindrical shape. As shown in FIG. 4, at least one of the electrically conductive elastomeric elements 116 may contact at least one of the first contact pads 128 of the sensor element 112 with a circumferential surface 132 of the electrically conductive elastomeric element 116.

The electrically conductive elastomeric elements 116, specifically, as shown in FIG. 4, cylindrically shaped electrically conductive elastomeric elements 116, such as for example elements or pieces that may comprise rubber, may be compressed axially specifically along a cylinder axis of the cylindrically shaped electrically conductive elastomeric element 116. The axial compression of the at least one electrically conductive elastomeric element 116 may allow contacting the sensor element 112 to an electronics unit 138. Particularly, the electrically conductive elastomeric elements 116 may have a Poisson's ratio v of 0.3 to 0.7, preferably of 0.4 to 0.6, more preferably of 0.5. Hence, an axial compression, specifically a compression in axial direction, of the electrically conductive elastomeric element 116, may lead to an increase of the diameter of the electrically conductive elastomeric element 116, e.g., the cylindrically shaped electrically conductive elastomeric element 116. In particular, the axial compression may lead to an expansion of the electrically conductive elastomeric element 116 in diameter. Thereby, it may be possible that a distance between eventually existing metal or metallic particles within the electrically conductive elastomeric element 116 may increase. For example, the metallic particles may move away from each other in radial direction due to the axial compression of the electrically conductive elastomeric elements 116, e.g., electrically conductive elastomeric elements 116 comprising an extruded material. Thus, an increased distance between metallic particles within the electrically conductive elastomeric elements 116 may decrease electrical conductivity or connectivity of the electrically conductive elastomeric elements 116 comprising metal particles. Thus, different types of electrically conductive materials may be used for forming the electrically conductive elastomeric elements 116. Specifically, the electrically conductive elastomeric element 116 may be made of or may comprise the electrically conductive material that is best suited or appropriate for fulfilling the imposed requirements or demands for the contact assembly 114. As an example, a preferred choice of material of the electrically conductive elastomeric elements 116 illustrated in the embodiment of the sensor element 110 shown in FIG. 4, may be a conductive rubber with an inherent conductive matrix material. For example, in case of electrically conductive elastomeric elements 116 comprising carbon filled rubber, each single contact to the sensor may show approximately 30 to 70 Ohms of resistance. For example, in some cases, a resistance of 30 to 70 Ohms of the electrically conductive elastomeric elements 116 may be sufficient for the task or may fulfill the imposed requirements for the contact assembly 114. If, for example, a lower resistance is required or necessary, a type of electrically conductive elastomeric element 116 comprising metallic particles in a conductive matrix may be a preferred choice. Again, the particles may lose contact between each other, as described above, in case of a non-conductive matrix. However, the conductive matrix may sustain over all connectivity, for example an overall connectivity from 0.5 to 3 Ohms at each contact point. Particularly, the high resistance matrix may bridge the distance, specifically very small gaps, between the metallic particles within the conductive matrix of the electrically conductive elastomeric element 116.

Figure 5:
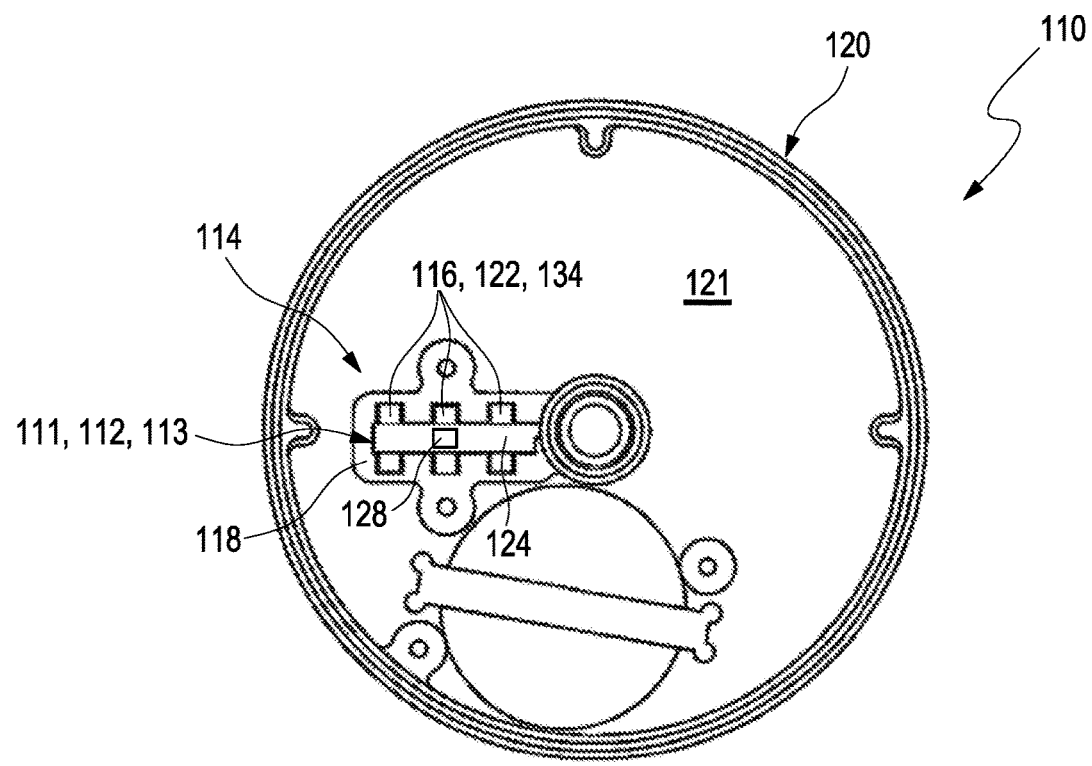
FIG. 5 shows a top plan view of a second embodiment of a sensor device.

In FIG. 5, a top plan view of a second embodiment of a sensor device 110 for detecting at least one analyte in a body fluid of a user is shown. The sensor device 110 comprises a contact assembly 114 for electrically interconnecting at least two modules 111, a first module 113 and a second module 115, illustrated in FIG. 6 and FIG. 7. The first module 113 comprises a sensor element 112. The sensor element 112 has at least one first contact pad 128. As shown in FIG. 5 the sensor element 112 may have three first contact pads 128. The first contact pads 128 may all be on a same side of the sensor element 112. However, as shown in FIG. 5, one first contact pad 128 can also be on a first side 124 of the sensor element 112. The remaining two first contact pads 128 may be on a second side 126 of the sensor element, which can not be seen in FIG. 5. The contact assembly 114 comprises three electrically conductive elastomeric elements 116 and a support structure 118. The sensor device 110 further comprises a housing patch 120, which may be configured for being mounted onto a skin of a user. As shown in FIG. 5, the electrically conductive elastomeric elements 116 are all arranged on the second side 126 of the sensor element 112. The sensor element 112 is clamped between at least two clamping elements 122. In this embodiment a first clamping element 134 comprises at least one of the electrically conductive elastomeric elements 116. A second clamping element 136, which is not shown in FIG. 5, may be the second module 115, comprising an electronics unit 138. The second module 115, e.g., the electronics unit 138, comprises at least one second contact pad 129, such as a contact area 140.

FIG. 6 shows a cross-sectional view of a medical device 142 for detecting at least one analyte in a body fluid of a user is shown. The medical device 142, as shown in FIG. 6, comprises the second embodiment of the sensor device 110, as shown in FIG. 5. The medical device 142 further comprises an insertion needle 144 for transcutaneously inserting the sensor element 112 at least partially into a body tissue of a user. The medical device 142 may further comprise a safety cap 146. The sensor element 112, specifically the first module 113, is clamped between the two clamping elements 122. The first clamping element 134 comprises the electrically conductive elastomeric elements 116. The second clamping element 136 is the electronics unit 138, specifically the second module 115. In this embodiment, the electronics unit 138 and the sensor device 110 may be pressed together, such that a pressure 148 is applied, symbolized in FIG. 6 by two arrows. When the pressure 148 is applied onto the electrically conductive elastomeric elements 116, the electrically conductive elastomeric elements 116 may be deformed, such that a possible distance between the second side 126 of the sensor element 112 and the electronics unit 138 may be filled. When the electrically conductive elastomeric elements 116 fill the distance between the second side 126 of the sensor element 112 and the electronics unit 138, the first contact pads 128, arranged on the second side 126 of the sensor element 112, and the second contact pads 129, e.g., the contact area 140, of the electronics unit 138 may be electrically connected. Thus the sensor element 112 and the electronics unit 138 are electrically connected by the deformed electrically conductive elastomeric elements 116.

FIG. 7 shows a perspective view of an embodiment of a contact assembly 114 interconnecting a first module 113 and a second module 115. The contact assembly 114 has at least one first contact pad, specifically three first contact pads 128, comprised by the first module 113. Further, the contact assembly 114 has at least one second contact pad 129, specifically three second contact pads 129, such as for example three contact areas 140, comprised by the second module 115. As illustrated in FIG. 7, the first contact pads 128 and the second contact pads 129 are arranged in a nonparallel fashion with respect to one another. For example, an angle between the surface of the at least one first contact pad 128 and the surface of the at least one second contact pad 129 deviates from 0° and deviates from 180°, e.g., by at least 5°, by at least 10° or by at least 20°.

The contact assembly 114 further comprises at least one electrically conductive elastomeric element 116 specifically, as illustrated in FIG. 7, the contact assembly 114 comprises three electrically conductive elastomeric elements 116.

Further, the contact assembly 114 is arranged such that one of the first contact pad 128 or the second contact pad 129 exerts a pressure 148 onto the electrically conductive elastomeric element 116. Preferably, as illustrated by the two arrows in FIG. 8, the second contact pads 129, specifically the contact areas 140, comprised by the second module 115, exert a pressure 148 onto the three electrically conductive elastomeric elements 116, thereby contacting the first contact pads 128 comprised by the first module 113. Specifically, the first module 113 comprises the sensor element 112 and the second module 115 comprises the electronics unit 138.

Figure 8:
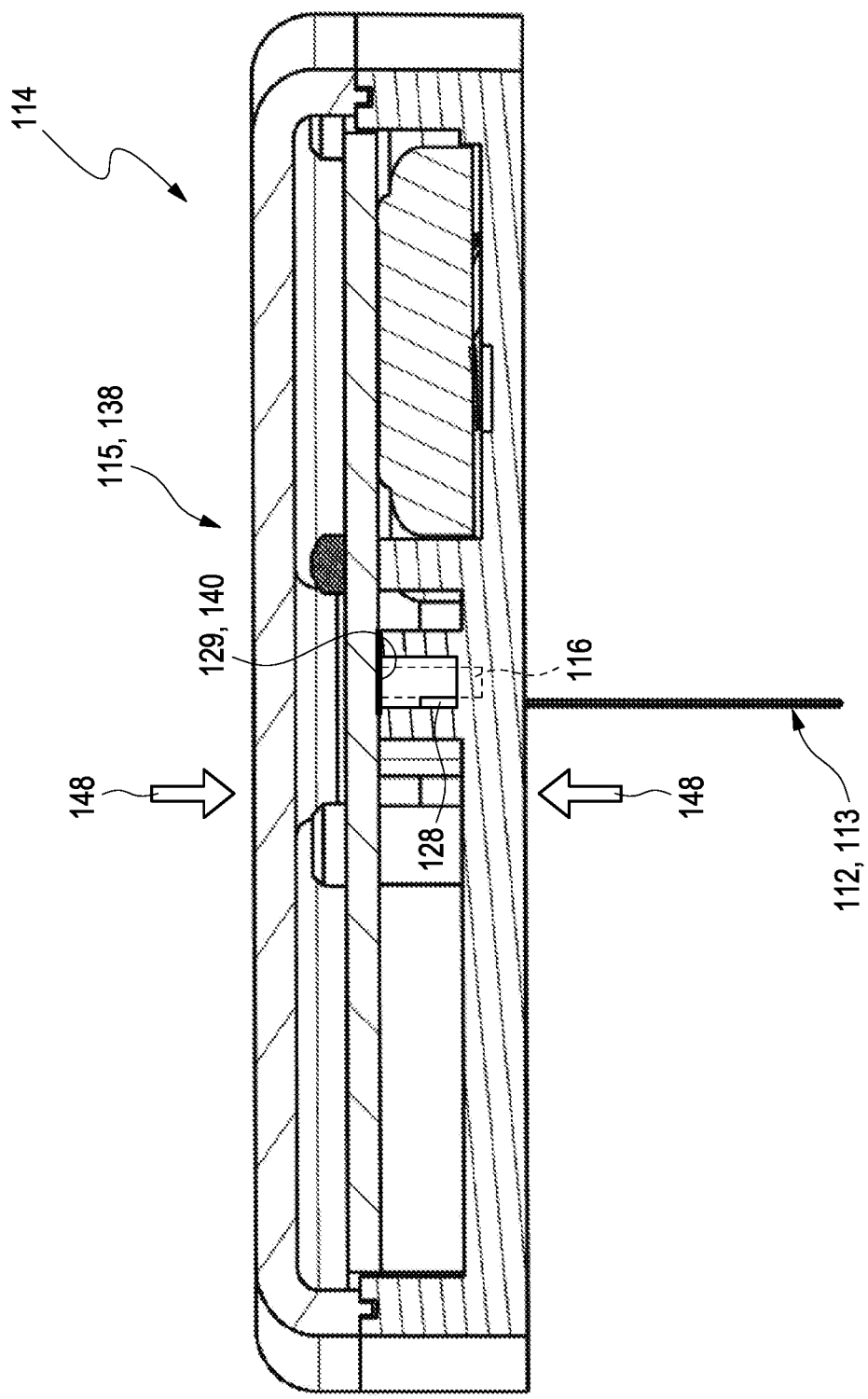
FIG. 8 shows a cross-sectional view of a sensor device for detecting at least one analyte in a body fluid of a user comprising a contact assembly.

FIG. 8 shows a cross-sectional view of a sensor device for detecting at least one analyte in a body fluid of a user comprising a contact assembly 114. As an example, the uncompressed electrically conductive elastomeric element 116 is illustrated in FIG. 8 in dashed lines. The exertion of the pressure 148, illustrated in FIG. 8 by two arrows, compresses the electrically conductive elastomeric element 116 into the shape illustrated in FIG. 8 in a solid line, thereby electrically interconnecting the first contact pad 128 of the first module 113, e.g., the sensor element 112, and the second contact pad 129 of the second module 129, e.g., the electronics unit 138. Specifically, the electrically conductive elastomeric element 116 is deformed such as to interconnect the first module 113 and the second module 115.

While exemplary embodiments have been disclosed hereinabove, the present invention is not limited to the disclosed embodiments. Instead, this application is intended to cover any variations, uses, or adaptations of this disclosure using its general principles. Further, this application is intended to cover such departures from the present disclosure as come within known or customary practice in the art to which this invention pertains and which fall within the limits of the appended claims.

LIST OF REFERENCE NUMBERS 110 sensor device
111 Module
112 sensor element
113 first module
114 contact assembly
115 second module
116 electrically conductive elastomeric element
118 support structure
120 housing patch
121 base plate
122 clamping element
123 Opening
124 first side
125 insertable portion
126 second side
127 contacting portion
128 first contact pad
129 second contact pad
130 Electrode
132 circumferential surface
134 first clamping element
136 second clamping element
138 electronics unit
140 contact area
142 medical device
144 insertion needle
146 safety cap
148 Pressure

What is claimed is:

1. A contact assembly, comprising:
a first module having a first contact pad;
a second module having a second contact pad, wherein the first and second contact pads are each planar contact pads and the first contact pad is arranged at a perpendicular angle to the second contact pad; and
an electrically conductive elastomer onto which one of the first and second contact pads exerts pressure in a first direction to thereby deform the electrically conductive elastomer, wherein deformation of the electrically conductive elastomer results in an expansion of an exterior surface of the electrically conductive elastomer in a second direction transverse to the first direction such that the other one of the first and second contact pads is contacted by the exterior surface of the electrically conductive elastomer to thereby electrically connect the first contact pad with the second contact pad.

2. The contact assembly according to claim 1, wherein the first module comprises a sensor for detecting an analyte.

3. The contact assembly according to claim 1, wherein the first contact pad is contacted by a first portion of the electrically conductive elastomer and the second contact pad is contacted by a second portion of the electrically conductive elastomer, wherein both the first contact pad and the second contact pad contact the exterior surface of the electrically conductive elastomer.

4. The contact assembly according to claim 3, wherein the electrically conductive elastomer has a cylindrical shape and the exterior surface defines a front face and a circumferential surface, wherein the pressure exerted in the first direction is exerted in an axial direction on the front face and the circumferential surface is thereby expanded in the second direction.

5. The contact assembly according to claim 1, wherein the electrically conductive elastomer comprises electrically conductive rubber.

6. A medical device for detecting an analyte, comprising:
a contact assembly, comprising:
a first module having a plurality of first contact pads;
a second module having a plurality of second contact pads, wherein
the plurality of first contact pads and the plurality of second contact pads are each planar contact pads and the plurality of first contact pads are arranged at a perpendicular angle to the plurality of second contact pads; and
a plurality of electrically conductive elastomer elements, wherein, for each electrically conductive elastomer element, one of the first and second contact pads exerts pressure to thereby deform the electrically conductive elastomer element, wherein deformation of the electrically conductive elastomer element results in the other one of the first and second contact pads being contacted by an exterior surface of the electrically conductive elastomer element whereby each of the electrically conductive elastomer elements electrically connects one of the plurality of first contact pads with one of the plurality of second contact pads;
wherein the first module comprises a sensor for electrochemically detecting the analyte, the sensor having first and second opposing sides wherein at least one of the plurality of first contact pads is located on the first side of the sensor and at least another one of the plurality of first contact pads is located on the second side of the sensor such that at least one of the electrically conductive elastomer elements is positioned adjacent to and contacts the at least one first contact pad on the first side of the sensor and another one of the electrically conductive elastomer elements is positioned adjacent to and contacts the at least another one of the first contact pads on the second side of the sensor; and
wherein the second module comprises an electronics assembly that has the plurality of second contact pads.

7. The medical device according to claim 6, wherein the contact assembly further comprises a support structure, wherein the plurality of electrically conductive elastomer elements is fully or partially embedded in the support structure, wherein the sensor is clamped between at least two of the plurality of electrically conductive elastomer elements.

8. The medical device according to claim 6, wherein the plurality of electrically conductive elastomer elements are clamped between the electronics assembly and the support structure, thereby being deformed and exerting a clamping force onto the sensor.

9. The medical device according to claim 6, wherein the electronics assembly comprises a printed circuit board having the plurality of second contact pads.

10. The medical device according to claim 6, wherein the sensor on the first side is contacted by two of the plurality of electrically conductive elastomer elements and wherein the sensor, on the second side opposing the first side, is contacted by one electrically conductive elastomer element which is disposed between the two electrically conductive elastomer elements contacting the first side.

11. The medical device according to claim 10 wherein each of the plurality of first contact pads and each of the plurality of second contact pads are contacted by the exterior surface of one of the plurality of electrically conductive elastomer elements;
wherein each of the plurality of electrically conductive elastomer elements has a cylindrical shape and the exterior surface of each electrically conductive elastomer element defines a front face and a circumferential surface, wherein each of the plurality of second contact pads exerts a pressure in an axial direction on the front face of a respective one of the plurality of electrically conductive elastomer elements to thereby expand the circumferential surface, in a direction transverse to the axial direction, of each of the plurality of electrically conductive elastomer elements; and
wherein the sensor is a planar element.

12. The medical device according to claim 6, wherein the plurality of first contact pads and the plurality of second contact pads are all pressed against exterior surfaces of the plurality of electrically conductive elastomer elements.

13. The medical device according to claim 6 wherein the sensor is clamped between two of the plurality of electrically conductive elastomer elements.

14. The medical device according to claim 6, further comprising an insertion needle for transcutaneously inserting the sensor.

15. A method for electrically interconnecting two modules, the method comprising:
providing a first module having a planar element with a first side and an opposite second side, the planar element having a plurality of first contact pads disposed thereon with at least one of the plurality of first contact pads being disposed on the first side and at least another one of the plurality of first contact pads being disposed on the second side;
providing a second module having a plurality of second contact pads;
providing a plurality of electrically conductive elastomer elements;
arranging the plurality of first contact pads and the plurality of second contact pads nonparallel to one another;
exerting pressure in a first direction onto the plurality of electrically conductive elastomer elements with the plurality of second contact pads to thereby deform the plurality of electrically conductive elastomer elements, wherein deformation of the plurality of electrically conductive elastomer elements results in an expansion of an exterior surface of each of the plurality of electrically conductive elastomer elements in a second direction transverse to the first direction such that the plurality of first contact pads are contacted by the exterior surfaces of the plurality of electrically conductive elastomer elements and each of the plurality of electrically conductive elastomer elements electrically connects one of the plurality of first contact pads with one of the plurality of second contact pads; and
wherein each of the plurality of first contact pads and each of the plurality of second contact pads are planar contact pads which are contacted by the exterior surface of one of the plurality of electrically conductive elastomer elements and the plurality of first contact pads are arranged at a perpendicular angle to the plurality of second contact pads.

16. The method according to claim 15 further comprising:
a) providing the planar element in the form of a sensor for electrochemically detecting the analyte, the sensor having the plurality of first contact pads; and
b) providing the second module with an electronics assembly having the plurality of second contact pads.

17. The method according to claim 15 wherein each of the plurality of electrically conductive elastomer elements has a cylindrical shape and the exterior surface of each electrically conductive elastomer element defines a front face and a circumferential surface, wherein each of the plurality of second contact pads exerts a pressure in an axial direction on the front face of a respective one of the plurality of electrically conductive elastomer elements to thereby expand the circumferential surface, in a direction transverse to the axial direction, of each of the plurality of electrically conductive elastomer elements.

* * * * *